US012812311B2

(12) United States Patent
Courtois

(10) Patent No.: US 12,812,311 B2
(45) Date of Patent: Nov. 24, 2026

(54) METHOD OF SELF-FITTING OF A BINAURAL HEARING SYSTEM

(71) Applicant: SONOVA AG, Staefa (CH)

(72) Inventor: Gilles Courtois, Uerikon (CH)

(73) Assignee: Sonova AG, Staefa (CH)

( * ) Notice: Subject to any disclaimer, the term of this patent is extended or adjusted under 35 U.S.C. 154(b) by 237 days.

(21) Appl. No.: 18/521,713

(22) Filed: Nov. 28, 2023

(65) Prior Publication Data

US 2024/0259742 A1 Aug. 1, 2024

(30) Foreign Application Priority Data

Jan. 30, 2023 (EP) .................................... 23153965

(51) Int. Cl.
*H04R 25/00* (2006.01)
*A61B 5/12* (2006.01)

(52) U.S. Cl.
CPC ............. *H04R 25/70* (2013.01); *A61B 5/125* (2013.01); *H04R 25/305* (2013.01); (Continued)

(58) Field of Classification Search
CPC ............ A61B 5/125; A61B 2562/0219; H04R 25/305; H04R 25/405; H04R 25/407; H04R 2225/39; H04R 2460/01
See application file for complete search history.

(56) References Cited

U.S. PATENT DOCUMENTS 5,825,894 A 10/1998 Shennib
9,848,273 B1 * 12/2017 Helwani .............. H04R 25/552
(Continued)

FOREIGN PATENT DOCUMENTS

WO WO-2005018275 A2 * 2/2005 ............. H04R 25/70
WO WO-2008025858 A2 * 3/2008 ............. G06F 3/165
(Continued)

OTHER PUBLICATIONS

Denino et al., "Cutting Through the Noise: Noise-Induced Cochlear Synaptopathy and Individual Differences in Speech Understanding Among Listeners With Normal Audiograms", Ear and Hearing, 2022, 43(1): 9-22.
(Continued)

*Primary Examiner* — Carolyn R Edwards
*Assistant Examiner* — Dylan Maguire Neece
(74) *Attorney, Agent, or Firm* — ALG Intellectual Property, LLC

(57) ABSTRACT

There is provided a method of self-fitting of a binaural hearing system worn by a user. The method comprises: implementing a present fitting configuration in the binaural hearing system; generating a spatialized binaural audio signal representative of a virtual auditory scene including at least a first audio source at a given angular position relative to the user; reproducing the spatialized binaural audio signal via the binaural hearing system to the user; instructing the user to turn the user's head towards the first audio source; measuring the respective head movement of the user via at least one motion sensor; estimating from the measured head movement the user's ability of spatial sound identification with the present fitting configuration of the binaural hearing system; and maintaining or modifying the present fitting configuration based on the estimated user's ability of spatial sound identification.

14 Claims, 3 Drawing Sheets

(52) U.S. Cl.
CPC ......... *H04R 25/405* (2013.01); *H04R 25/407* (2013.01); *A61B 2562/0219* (2013.01); *H04R 2225/39* (2013.01); *H04R 2225/43* (2013.01); *H04R 2460/01* (2013.01)

(56) References Cited

U.S. PATENT DOCUMENTS

| | | | | |
|---|---|---|---|---|
| 2002/0107692 | A1* | 8/2002 | Litovsky ................ | A61B 5/121 704/E13.008 |
| 2010/0310101 | A1* | 12/2010 | Anderson ............... | H04S 7/301 381/314 |
| 2011/0075853 | A1* | 3/2011 | Anderson ............ | A61B 5/6814 381/60 |
| 2014/0241537 | A1 | 8/2014 | Krause et al. | |
| 2015/0023535 | A1 | 1/2015 | Shennib | |
| 2017/0070833 | A1 | 3/2017 | Shennib | |
| 2017/0332186 | A1* | 11/2017 | Riggs ...................... | H04S 3/008 |
| 2018/0227690 | A1 | 8/2018 | Lyren et al. | |
| 2019/0166440 | A1 | 5/2019 | Vries et al. | |
| 2021/0243535 | A1 | 8/2021 | Krause | |
| 2021/0409876 | A1 | 12/2021 | Hildebrand | |
| 2022/0191625 | A1 | 6/2022 | Wiedenbrueg et al. | |

FOREIGN PATENT DOCUMENTS

| | | | |
|---|---|---|---|
| WO | 2010117712 | A2 | 10/2010 |
| WO | 2020214482 | A1 | 10/2020 |

OTHER PUBLICATIONS

Edwards B., "Emerging Technologies, Market Segments, and MarkeTrak 10 Insights in Hearing Health Technology", Semin Hear 2020; 41(1): 37-54.

Extended European Search Report sent in application 23153965.1, mailed on Jul. 4, 2023.

Leslie, M., "New US Rules Promise to Unlock Hearing Aid Availability", Engineering, 2022, 14(7):7-9.

* cited by examiner

METHOD OF SELF-FITTING OF A BINAURAL HEARING SYSTEM

RELATED APPLICATIONS

The present application claims priority to EP Patent Application No. 23153965.1, filed Jan. 30, 2023, the contents of which are hereby incorporated by reference in their entirety.

BACKGROUND INFORMATION

The availability and dissemination of non-prescriptive hearing devices offering hearing loss compensation and speech enhancement, such as over-the-counter (OTC) hearing aids or consumer earbuds, are expected to substantially grow in the coming years (cf. Leslie, M., "New US Rules Promise to Unlock Hearing Aid Availability", Engineering, 2022, 14(7):7-9). As no hearing care professional is involved in the fitting of those devices, a prominent challenge is to ensure that users are offered a tuning of the sound processing capabilities of the devices in a relevant and satisfying way. This procedure is referred to as "self-fitting". Multiple self-fitting principles are known.

According to one example a pure-tone hearing test is provided and the gain and compression curves are calculated accordingly; this is available in commercial devices such as Apple AirPods Pro, Jabra Enhance Plus and Nuheara IQbuds2 MAX.

According to WO 2020/214482 A1 a questionnaire is provided to the user of a hearing aid from which a score is derived and mapped to a pure tone average and speech recognition performance.

According to US 2019/0166440 A1 two stimuli modified by different sound processing are presented to the user of a hearing aid and the user is requested to indicate a preference; this procedure is iterated until it converges to an optimal and personal fitting.

According to US 2022/191625 A1 multiple environmental situations are shown to the user of a hearing aid on a display without sound, so that the user can rate the relevance and report hearing difficulties encountered in every scene; a hearing loss class is associated with each situation, which steers the fitting of the hearing aids.

According to US 2017/0070833 A1 audio signals from a fitting soundscape are presented to the user of a hearing aid at loud and soft levels and fitting is performed in-situ based on the user's perceptual assessment of the output of the hearing aid.

According to US 2021/243535 A1 speech samples are synthesized and altered for testing or optimizing hearing device parameters.

WO 2005/018275 A2 relates to fitting of hearing devices, wherein speech audio samples including semantics are presented to the user for being recognized by the user who then speaks back the recognized sentences/words/syllables; the system may test user's own speech production. A similar fitting method is described in WO 2010/117712 A2, wherein stimuli which may e.g. include VCV nonsense words are sent to a user and the user's response is measured.

According to WO 2008/025858 A2 a hearing care professional adjusts the parameter setting of a hearing system according to user feedback on spatial perception of audio sequences from real life sound sources reproduced via the hearing system; in addition, the user may be provided synchronously with the audio sequence with a visualization of a scene to which said audio sequence belongs.

EP 3 930 350 A1 describes acoustic representation of a virtual environment which may comprise a plurality of sources, such as multiple people speaking, which all may be represented such that their location can be perceived realistically.

US 2014/241537 A describes the detection by a hearing device user of e.g. transitions between different phonems to indicate a hearing performance.

US 2018/0227690 A1 relates to a method of generating spatial audio signals for earphones coupled with a handheld portable electronic device, wherein coordinates of a location of the handheld portable electronic device with respect to the user are determined and this location is saved as a sound localization point. During the telephone call, a voice of another person is convolved so the voice externally localizes to the person as a binaural sound at the sound localization point.

BRIEF DESCRIPTION OF THE DRAWINGS

Hereinafter, examples of the invention will be illustrated by reference to the attached drawings, wherein.

DETAILED DESCRIPTION

Figure 1:
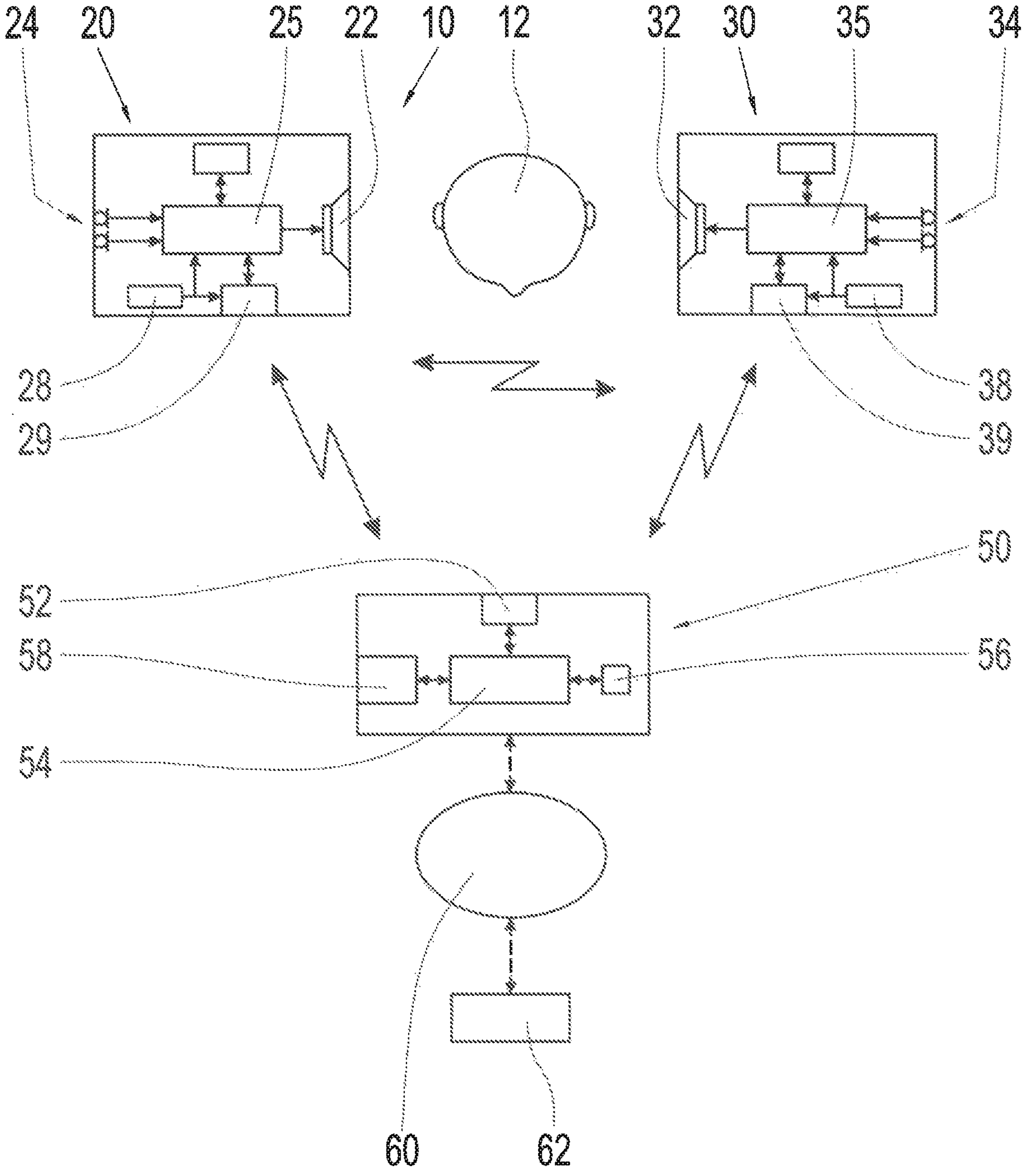
FIG. 1 is a schematic representation of an example of a self-fitting arrangement comprising a binaural hearing system and an accessory device.

Described herein is a method of self-fitting of a binaural hearing system.

Embodiments described herein provide for a method of self-fitting of a binaural hearing system which allows to substantially preserve the user's spatial sound identification ability. It is a further feature to provide for a corresponding self-fitting arrangement.

The embodiments described herein are beneficial in that, by monitoring the user's ability of spatial sound identification during the fitting process by using a motion sensor of the binaural hearing system, a negative impact of certain fitting configurations on the user's ability of spatial sound identification can be easily recognized, so that user's ability of spatial sound identification can be preserved, for example by excluding such detrimental fitting configurations.

According to one example, the method may ne iterated for different fitting configurations so as to optimize the fitting configuration regarding the user's ability of spatial sound identification by minimizing the deviation between an expected head movement and the measured head movement.

According to one example, the virtual auditory scene may include a second audio source arranged at a second angular position relative to the user, wherein the user is instructed to turn the head towards the second audio source, wherein the respective head movement of the user is measured via the at least one motion sensor, and wherein the user's ability of spatial sound identification with the present fitting configuration of the hearing system is estimated from the measured head movement. For example, the first audio source may be a target talker and the second audio source may be a competing talker. In addition, the virtual auditory scene may include diffuse noise.

According to one example, the parameters of the virtual auditory scene, in particular levels, distances and/or yaw angles of the first audio source and/or the second audio source and/or the level of diffuse noise, may be varied for performing different head movement measurements.

According to one example, the user may be instructed via instruction audio signals reproduced by the binaural hearing system.

According to one example, the user may provide voice feedback to the instruction audio signals which is recognized via automatic speech recognition. For example, the automatic speech recognition may recognize words from a database limited to not more than 200 words. Further, each of the hearing devices may comprise a microphone arrangement for capturing the user's voice feedback. For example, the capturing of the user's voice feedback may utilize acoustic beamforming and/or extraction of speech features based on previous recordings of the user's voice. The binaural hearing system may transmit audio signals representative of the user's voice feedback to an accessory device which performs the automatic speech recognition. The instruction audio signals may include key words presented by the first audio source, wherein the user may be instructed to repeat the key words, and wherein the voice feedback may include the repetition of the key words by the user.

According to one example, prior to the start of the measuring of head movements the user may undergo a calibration process to provide an absolute reference for the head movements.

According to one example, the at least one motion sensor may comprise a first inertial sensor in the first hearing device and a second inertial sensor in the second hearing device. For example, the first and second inertial sensors may comprise accelerometers and/or gyroscopes. Further, each hearing device may include a magnetometer for assisting the inertial sensors.

According to one example, the spatialized binaural audio signal may be generated by using a default set of head related transfer functions (HRTFs). According to another example, the spatialized binaural audio signal may be generated by using a set of generic HRTFs selected from a plurality of pre-sets such that it matches best with the user's perception. According to a further example, the spatialized binaural audio signal may be generated by using a set of HRTFs measured using the binaural hearing system worn by the user and an accessory device.

According to one example, fitting parameters of the fitting configuration may include an amount of wide dynamic range compression, as determined by the compression kneepoints, beamformer pattern, an amount of noise reduction, and/or an amount of reverberation reduction.

According to one example, the generating of the spatialized binaural audio signal representative of the virtual auditory scene; the estimating, from the measured head movement, the user's ability of spatial sound identification with the present fitting configuration of the hearing system; and/or the assessing the present fitting configuration based on the estimated user's ability of spatial sound identification with the present fitting configuration may be performed on an accessory device communicatively coupled with binaural hearing system. For example, the accessory device may be a smartphone.

A "hearing device" as used hereinafter is any ear level element suitable for reproducing sound by stimulating a user's hearing, such as an electroacoustic hearing aid, a bone conduction hearing aid, an active hearing protection device, a hearing prostheses element such as a cochlear implant, a wireless headset, an earbud, an earplug, an earphone, etc.

A certain "fitting configuration" of the binaural hearing system as used hereinafter is a certain setting of values of fitting parameters, i.e., audio signal processing parameters, such as compression kneepoints, the amount of noise reduction and/or beamformer pattern.

A "spatialized binaural audio signal" is as used hereinafter an audio signal which, when reproduced by the binaural hearing system to the user, creates a spatial sound perception by the user.

A user's "ability of spatial sound identification" as used hereinafter is the ability of the user to identify perceived directions of sound sources in a spatialized binaural audio signal reproduced by the binaural hearing system worn by the user.

A user's "ability of spatial sound segregation" as used hereinafter is the ability of the user to discriminate two adjacent (with regard to their angular position, in particular with regard to azimuth) sound sources in a spatialized binaural audio signal reproduced by the binaural hearing system worn by the user as separate sound sources.

It is expected that the main consumers for OTC hearing aids, as well as consumer earbuds with speech enhancement features, are those with a self-declared hearing disorder; these self-reported hearing difficulties are mostly coming from individuals with hidden hearing loss and to a lesser extent to mild/moderate losses (cf., for example, Edwards B., "Emerging Technologies, Market Segments, and MarkeTrak 10 Insights in Hearing Health Technology", Semin Hear 2020; 41(1): 37-54).

It is well documented that traditional hearing tests (e.g. audiogram) are suboptimal to fit hearing devices in an adequate way for those with a hidden hearing loss. As an example, some specific suprathreshold tasks have been shown to elicit significant difficulties in individuals with hidden hearing loss, such as extracting the voice of a speaker of interest in competing spatially-separated speech streams (i.e., spatial release from masking). This is hypothesized to come from some impairment in the time processing performed by the auditory system, such as pitch discrimination and fine sound localization (see DeNino et al., "Cutting Through the Noise: Noise-Induced Cochlear Synaptopathy and Individual Differences in Speech Understanding Among Listeners With Normal Audiograms", Ear and Hearing, 2022, 43(1): 9-22.for a review).

A self-fitting approach based on spatial sound, in particular speech, identification or segregation is expected to be of particular efficiency to optimize fitting of hearing device parameters. Such approach may be supported by the following measures: (1) presenting consistent stimuli through the hearing devices to the user, (2) tracking responsive head motion of the user by using inertial sensors of the hearing devices, and (3) collecting user feedback in a way which does not demand the user to look at a screen during the self-fitting time.

FIG. 1 is a schematic representation of an example of a self-fitting arrangement comprising a binaural hearing system 10 and an accessory device 50 which are communicatively coupled via wireless links 60.

The binaural hearing system 10 comprises a first hearing device 20 including a first output transducer 22 for stimulating a first ear of a user 12 and a second hearing device 30 including a second output transducer 32 for stimulating a second ear of the user. The hearing devices 20, 30 are communicatively coupled via a wireless binaural link 62. Each of the hearing devices 20, 30 further comprises a microphone arrangement 24, 34 for capturing audio signals from ambient sound, an audio signal processing unit 25, 35 for processing the captured audio signals according to a present fitting configuration stored in a memory 26, 36, an inertial sensor 28, 38 and a wireless interface 29, 39 for establishing the wireless links 60, 62.

The audio signal processing unit may apply acoustic beamforming, a hearing loss dependent gain model including suitable compression, such as wide dynamic range compression (WDRC), noise reduction, reverberation reduction, etc. Parameters of such audio signal processing include, for example, compression kneepoints, the amount of noise reduction, beamformer pattern, amount of wide dynamic range compression and reverberation reduction strength. Also the output of the inertial sensors 28, 38 may be used in the audio signal processing. The hearing devices may coordinate their audio signal processing by exchanging data and/or audio signals via the binaural link 62. The processed audio signals are reproduced, after amplification, by the output transducers 22, 32 to the user 12.

The inertial sensors 28, 38 act as motion sensors of the binaural hearing system 10. While in the present example each of the hearing devices 20, 30 comprises a separate motion/inertial sensor, there may be examples in which a single motion sensor of binaural hearing system is sufficient, in which case only of one of the hearing devices 20, 30 would include a motion/inertial sensor.

The accessory device 50 comprises wireless interface 52 for establishing the wireless link 60 with the hearing devices 20, 30, a processing unit 54, a memory 56, and a user interface 58, such as a touchscreen, for the user 12. The accessory device 50 also may comprise an interface 59 for connecting via the internet 60 to a server 62 of the manufacturer of the hearing devices 20, 30 for downloading a self-fitting app and/or data required for conducting a self-fitting procedure of the hearing devices 20, 30. According to one example, the accessory device 50 may be a smartphone.

In the self-fitting procedure, a present fitting configuration 10 is implemented in the binaural hearing system by setting certain values of the respective audio signal processing parameters in the binaural hearing system 10, for example in the memories 26, 36 of the hearing devices 20, 30. A spatialized binaural audio signal representative of a virtual auditory scene including at least a first audio source arranged at a first position relative to the user is generated, for example in the accessory device 50, and is reproduced to the user 12 via the output transducers 22, 32 of the hearing devices 20, 30 (the spatialized binaural audio signal may be transmitted to the hearing devices 20, 30 via the wireless link 60). Further, an instruction audio signal instructing the user to turn the head towards the first audio source is generated (for example in the accessory device 50) and is reproduced to the user 12 via the output transducers 22, 32 of the hearing devices 20, 30. The position of the audio source relative to the user may be characterized by the angular position relative to the user and the distance from the user, wherein the angular position is determined by azimuth (yaw) and the elevation (pitch). Typically, the elevation will be less relevant than the azimuth and may relatively small and substantially constant in the tests, i.e., in many cases the virtual auditory scene may be substantially located in a horizontal plane.

Then the resulting head movement of the user 12 (which typically will be substantially a yaw head movement) is determined via the first and second inertial sensor 28, 38 (for example, the respective sensor signals may be sent via the wireless link 60 to the accessory device 50 where the head movement is calculated). From the measured head movement the user's ability of spatial sound identification with the present fitting configuration of the hearing system can be estimated by comparing the measured head movement with the angular position of the first audio source in the virtual auditory scene. The inertial sensors 28, 38 may be formed by accelerometers and/or gyroscopes; further, each hearing device 20, 30 may include a magnetometer for assisting the inertial sensors 28, 38.

The present fitting configuration then may be assessed based on the estimated user's ability of spatial sound identification with the present fitting configuration, and, depending and the result of the assessment, the present fitting configuration may be maintained (if the result is satisfactory) or it may be modified (if the result indicates that the user's ability of spatial sound identification is deteriorated by the present fitting configuration).

Figure 2:
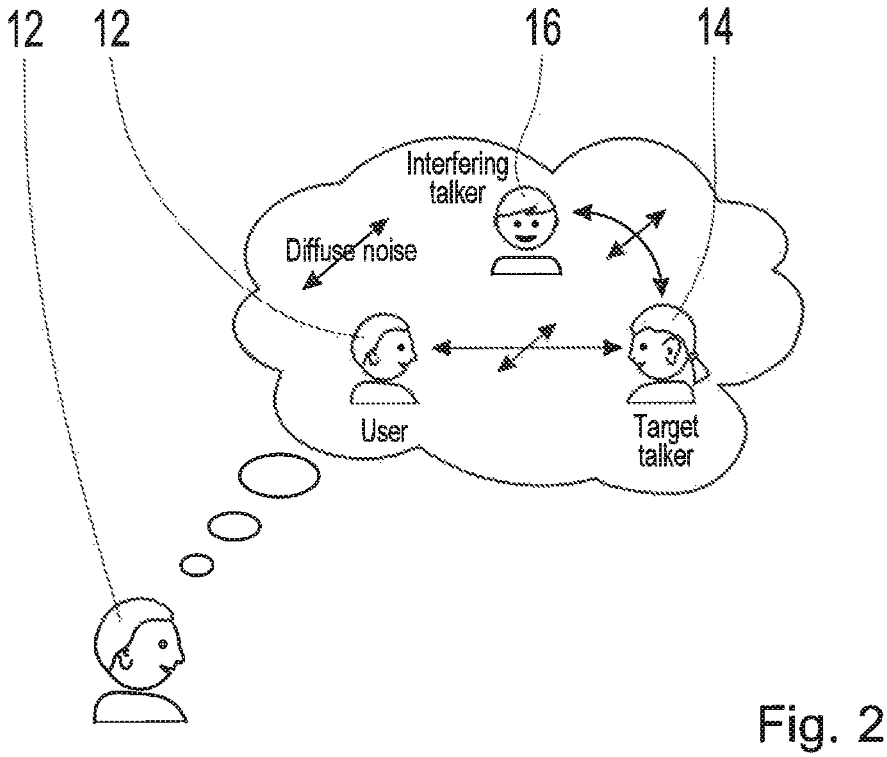
FIG. 2 is a schematic illustration of a virtual auditory scene provided to the user of the binaural hearing system during self-fitting.
Figure 3A:
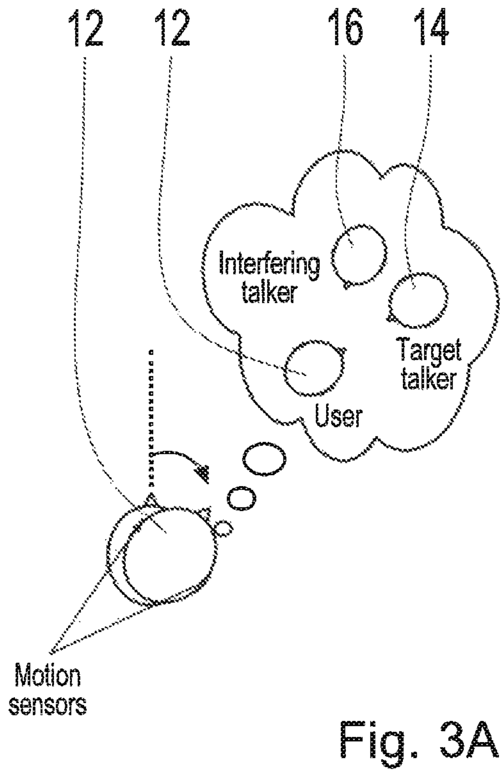
FIGS. 3A-3B illustrate an example of a spatial sound identification and sound source segregation task carried out by the user binaural hearing system during self-fitting.

An example of such self-fitting procedure is illustrated in FIGS. 2 and 3A, B, wherein FIG. 2 shows an example of a typical virtual scene that is synthesized as a spatialized binaural audio signal. When such spatialized binaural audio signal is reproduced, the user 12 perceives a virtual environment which may contain at least three components: a target talker 14 (forming a first audio source oriented at first angle—as already mentioned above, in many cases the yaw will be much more important than the pitch—and at a first distance relative to the user 12), the speech of whom conveys the message the user has to focus on, a competing talker 16 spatially separated from the target talker 14 (forming a second audio source oriented at second angle and at a second distance relative to the user 12), the speech of whom is interfering with the target talker 14, and some diffuse noise, such as babble noise. Such scene is typically encountered in a bar or a restaurant, where the understanding of speech is challenged.

Figure 4:
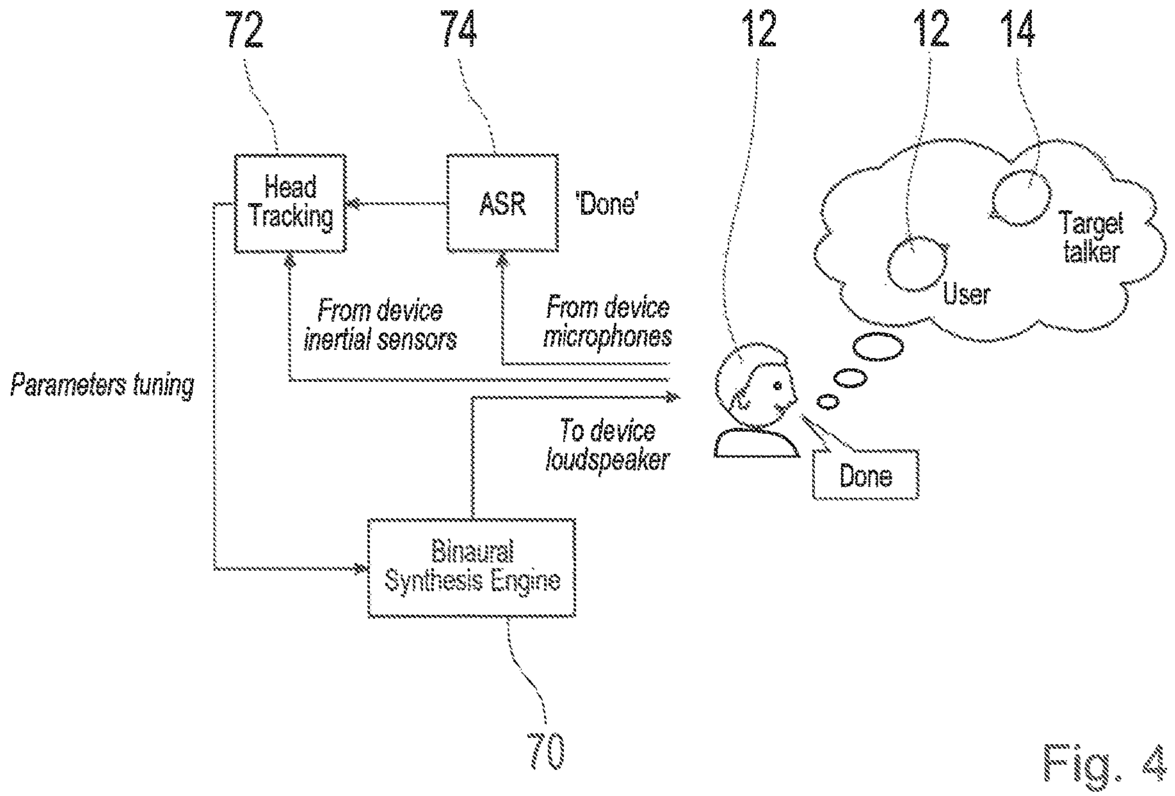
FIG. 4 is a schematic illustration of an example of the use of automatic speech recognition during self-fitting.
Figure 5:
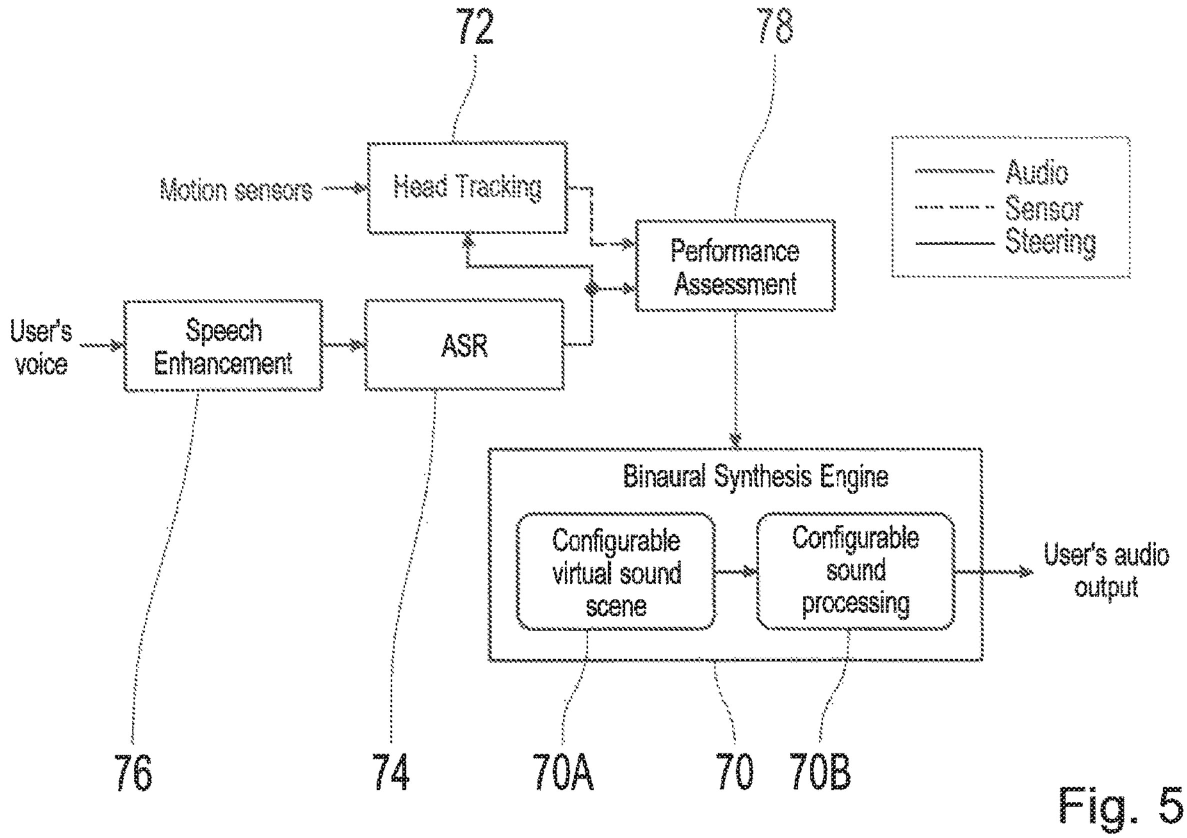
FIG. 5 is a schematic illustration of an example of a self-fitting method for a binaural hearing system.

The spatialization of the sound sources 14, 16 can be achieved using generic spatial filters by a so-called binaural synthesis engine 70 (see FIGS. 4 and 5). A default HRTF (Head Related Transfer Function) set may be used for every user. Alternatively, the user may first select a set of generic HRTFs among multiple available pre-sets so that the simulated location of the selected set match the location that the user perceives. According to a further alternative, the HRTFs of the user may be recorded via a measurement mechanism relying on the hearing devices and a smartphone, as shown, for example, in US 2018/0227690 A1. It is noted that a selected set of well-matching HRTFs may be used for other purposes, such as creating 3D sound effect in streaming, as already offered by Apple AirPods Pro.

The parameters characterizing the virtual auditory scene may be systematically varied so as to implement different virtual auditory scenes. In particular, the angle (in particular, the yaw) and the distance between the user and the talkers 14, 16, the speech levels of the talkers 14, 16 and the diffuse noise level may be varied for optimizing the self-fitting process.

Spatial identification and segregation are key processes in the intelligibility of speech in real environments. Inappropriate settings of certain fitting parameters may have a negative impact on the spatial identification and segregation capability of the user. For example, wide dynamic range compression (WDRC) used in hearing devices is known to decrease the interaural level difference, which is a cue used by the auditory system to localize sound sources in space. An excessive WDRC strength may therefore impair the ability of the user to perform sound segregation. Thus, the amount of WDRC should be adjusted in a way that the speaker segregation performance of the user is preserved (in practice, the amount of WDRC is determined by the compression kneepoint, so that the amount of WDRC can be adjusted by adjusting the compression kneepoint accordingly). Similarly, excessive WDRC and/or reverberation reduction algorithm strength may lead to poorer speaker discrimination in distance. The associated parametrization hence should be in a way so as to ensure that the distance discrimination capabilities of the user are preserved. Also certain beamformer patterns may rely on the ability of the user to discriminate spatially-separated sound sources.

In the present self-fitting method the user's ability of spatial sound identification may be monitored during the fitting process by presenting a virtual auditory scene to the user so as to assess the respective fitting configuration regarding its performance for preserving the user's ability of spatial sound identification. Thereby deterioration of the user's ability of spatial sound identification as a result of an inappropriate fitting parameter setting can be avoided. In addition, also the user's ability of spatial sound segregation may be monitored during the fitting process by using the virtual auditory scene so as to assess the respective fitting configuration also regarding its performance for preserving the user's ability of spatial sound segregation.

For example, the amount of WDRC (by adjusting compression kneepoints) and/or the amount of reverberation reduction and/or the amount of noise reduction and/or beamformer pattern may be set in a way that preserves or even improves the user's ability of spatial sound identification.

Figure 3B:
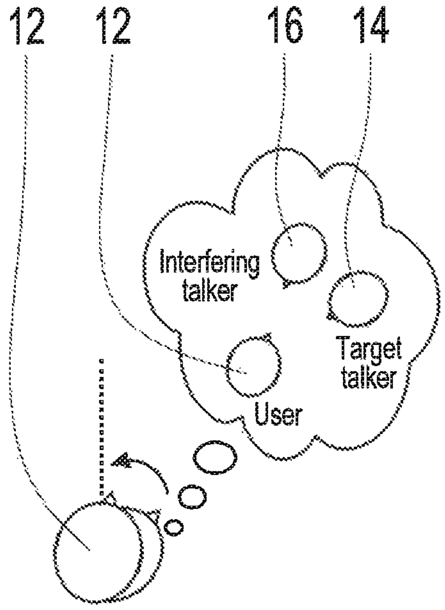

An example of head movement tracking for assessment of the ability of a user 12 to spatially discriminate a target talker 14 and an interfering/competing talker 16 is illustrated in FIGS. 3A,B, wherein the user 12 is instructed, by an appropriate audio signal presented via the hearing devices 20, 30, to first look in the direction of the target talker 14 (see FIG. 3A) and then in the direction of the competing talker 16 (see FIG. 3B). The resulting head rotation is measured via the inertial sensors 28, 38 and is compared to the angular positions of the talkers 14, 16 in the virtual auditory scene. The degree of deviation of the measured head rotation is indicative of the user's ability of spatial sound identification: little deviation indicates good spatial sound identification ability, while large deviation indicates poor spatial sound identification ability. This concept does not require speech understanding tests; rather, it is sufficient that the user can identify the direction/position of the respective (virtual) talker 14, 16. It is noted that a head tracking algorithm usually will require the user 12 to first go through a calibration process to provide the system with an absolute reference (e.g. pointing to the front to define the 0° orientation).

In addition, the virtual auditory scene may be also used to assess the user's ability of spatial sound segregation with the respective fitting configuration. To this end, the angle between the sound sources/talkers 14 and 16 may be varied so as to find minimum angle between them which still allows the user to perceive the sound sources 14, 16 as spatially separate sound sources. This minimum angle is indicative of the user's ability of spatial sound segregation: the smaller this angle is, the better is the user's ability of spatial sound segregation.

During the self-fitting procedure, and in particular during the assessment of the user's ability of spatial sound identification, any interaction of the user with the accessory device 50 resulting in head movement should be avoided so as to not interfere with the head rotation measurements. Thus, the instructions to the user 12 should be provided acoustically via the hearing devices 20, 30. Further, also the user's feedback to tests may be provided acoustically to the hearing devices 20, 30 and the accessory device.

For example, the user 12 may provide voice feedback to the instruction audio signals which is recognized via automatic speech recognition (ASR), which, as such, is a well-established technique with various commercial applications, like smartphones or user control systems in cars. An example of such user feedback is schematically illustrated in FIG. 4, wherein the user 12 indicates by speaking the word "done" that that he/she has finalized the previously instructed task of pointing the head towards the (virtual) target talker 14, so that the self-fitting procedure can be continued. Such voice feedback eliminates a need of the user to look towards the accessory device 50, thereby avoiding head movements not caused by the instructions of the self-fitting process.

In addition, ASR may be used for conducting speech understanding tests with the user 12 when listening to the virtual auditory scene, wherein the virtual target talker 14 presents key words with or without the presence of an interfering talker 16 and/or diffuse noise, wherein the user 12 is instructed to repeat the key words and wherein the user's voice feedback including the repetition of the key words undergoes ASR so as to recognize whether the user correctly understands the key words. The key words can comprise syllables or words that are generally easily misrecognized acoustically as e.g. "immigrate/emigrate". The key words can form key phrases including semantics wherein the user is required to speak back the whole key phrases. Also in this case the use of ASR allows the user to provide feedback without having to interact, for example, with a display of the accessory device 50, thereby avoiding undesired head movements.

Since ASR works particularly well when the system must recognize words from a limited database, the words to be recognized may be limited specifically, for example to not more than 200 words.

The user's voice feedback may be captured by the microphone arrangements 24, 34 of the hearing devices 20, 30; the capturing of the user's voice feedback may utilize acoustic beamforming (which may be implemented in the audio signal processing unit 25, 35), so as to increase the SNR of the captured audio signals. The captured user's voice feedback, i.e. the processed audio signals as provided by audio signal processing unit 25, 35, may be transmitted via the wireless link 60 the to the accessory device 50 which then performs the ASR. Extraction of speech features based on previous recordings of the user's voice may be utilized to improve ASR.

A schematically illustrated in FIG. 4, the binaural synthesis engine 70 generates the virtual auditory scene and the instructions presented to user 12 via the output transducers 22, 32 of the hearing devices 20, 30. The user 12 responds to such audio stimuli by head movement detected by the inertial sensors 28, 38 of the hearing devices 20, 30 and/or by voice feedback captured by the microphone arrangements 24, 34 of the hearing devices 20, 30. The output of the inertial sensors 28, 38 is supplied to a head tracking unit 72 which determines head movements, and the audio signals representative of the user's voice feedback provided by the hearing devices 20, 30 are supplied to an ASR unit 74 for recognizing the words/speech contained in the audio signals. The output of the ASR unit 74 is supplied to the head tracking unit 72 so that the head tracking unit 74 can recognize, for example, when the user has finalized a given task. The output of the head tracking unit 72 is used for assessment of the present fitting configuration and for respective adjustment of the audio signal processing parameters used by the binaural synthesis engine 70.

A slightly more detailed schematic illustration of an example of a self-fitting procedure is shown in FIG. 5.

The user's voice is captured by the hearing device microphones 24, 34, possibly using a beamformer. The associated audio signals may be processed to extract speech features only (for example, previous recordings of the user's voice can drive this enhancement), as indicated by a speech enhancement unit 76. The processed audio signals then are supplied to the ASR unit 74, which identifies keywords of a closed set or the indication from the user that the direction identification task has been performed. The signals of the motion/inertial sensors 28, 38 are processed in the head tracking unit 72 to determine the user's head yaw and track the rotation of the user's head in real-time.

The outputs of the ASR unit 74 and head tracking unit are supplied as input to a performance assessment unit 78 which determines, based on these inputs, performance of the user (with the present fitting configuration and with the present virtual auditory scene) is estimated, such as the ability to correctly repeat key words in a given simulated environment (i.e., in the given virtual auditory scene), the ability to point in the direction of the target talker 14 and/or interfering talker 16 with a given set of sound processing parameters (i.e., the present fitting configuration), etc. Depending on the estimated user's performance, some parameters of the virtual auditory scene (indicated at unit 70A, e.g., distance between user 12 and target talker 14, angle between interfering talker 16 and target talker 16, etc.) and/or some parameters of the hearing device audio signal processing (indicated at unit 70B, e.g., compression kneepoints, amount of noise reduction, beamformer pattern, etc.) are adjusted to provide a new binaural audio output to the user's ears. The process is reiterated until it converges to an optimal fitting that maximizes the estimated performance of the user.

It is noted that most of the signal processing can be externalized on the accessory device 50 to reduce battery consumption in the hearing devices 20, 30 and get access to more processing power; this includes, for example all blocks/units illustrated in grey in FIG. 5, namely, speech enhancement (unit 76), ASR (unit 74), head tracking (unit 72), performance assessment (unit 78) and generation of the virtual auditory scene (unit 70A).

The self-fitting method may be implemented by installing a corresponding app on the accessory device 50. When having started a self-fitting procedure, the app may generate a virtual auditory scene by providing the respective binaural audio signals. The app then transmits the virtual auditory scene (i.e., the binaural audio signals) to the hearing devices and provide them with a set of parameters to be tested. Left and right hearing devices 20, 30 process the wirelessly transmitted audio signals with the provided set of parameters. Left and right hearing devices reproduce the sound in the ear of the user based on the processed audio signals. The head motion and voice of the users are sensed by the motion sensors of the hearing devices, and the associated signals are transmitted wirelessly to the app. The app determines if the feedback from the users is as expected or not. Then it goes back the starting point with a new virtual auditory scene and/or a new hearing device parameter set.

What is claimed is:

1. A method of self-fitting of a binaural hearing system worn by a user, comprising a first hearing device including a first output transducer for stimulating a first ear of the user, and a second hearing device including a second output transducer for stimulating a second ear of the user, the binaural hearing system further comprising at least one motion sensor, the method comprising:

implementing a present fitting configuration in the binaural hearing system;

generating a spatialized binaural audio signal representative of a virtual auditory scene including at least a first audio source at a given angular position relative to the user and a second audio source arranged at a second angular position relative to the user;

reproducing the spatialized binaural audio signal via the binaural hearing system to the user;

instructing the user to turn the user's head towards the first audio source;

instructing the user to turn the user's head towards the second audio source;

measuring respective head movements of the user via the at least one motion sensor;

determining, from the measured head movements, a deviation between the measured head movements and expected head movements corresponding to the angular positions of the first audio source and the second audio source in the virtual auditory scene;

estimating from the measured head movements the user's ability of spatial sound identification with the present fitting configuration of the binaural hearing system, the estimating of the user's ability of spatial sound identification including estimating the user's ability of spatial sound segregation based on the determined deviation and a variation of an angle between the first audio source and the second audio source so as to determine a minimum angular separation at which the user perceives the first audio source and the second audio source as separate sound sources; and maintaining or modifying the present fitting configuration based on the estimated user's ability of spatial sound identification.

2. The method of claim 1, wherein the method is iterated for different fitting configurations so as to optimize the fitting configuration regarding the user's ability of spatial sound identification by minimizing a deviation between an expected head movement and the measured head movements.

3. The method of claim 1, wherein the first audio source is a target talker and the second audio source is a competing talker.

4. The method of claim 1, wherein the virtual auditory scene includes diffuse noise.

5. The method of claim 1, wherein parameters of the virtual auditory scene including at least one of levels, distances, yaw angles of at least one of the first audio source or the second audio source, or the level of diffuse noise, are varied for performing different head movement measurements.

6. The method of claim 1, wherein the user is instructed via instruction audio signals reproduced by the binaural hearing system.

7. The method of claim 6, wherein the user provides voice feedback to the instruction audio signals which is recognized via automatic speech recognition.

8. The method of claim 7, wherein each of the hearing devices comprises a microphone arrangement for capturing the user's voice feedback, and wherein the binaural hearing system transmits audio signals representative of the user's voice feedback to an accessory device which performs the automatic speech recognition.

9. The method of claim 7, wherein the instruction audio signals include key words presented by the first audio source, wherein the user is instructed to repeat the key words, and wherein the voice feedback includes repetition of the key words by the user.

10. The method of claim 1, wherein the at least one motion sensor comprises a first inertial sensor in the first hearing device and a second inertial sensor in the second hearing device, and wherein the first inertial sensor and the second inertial sensor comprise at least one of accelerometers or gyroscopes.

11. The method of claim 1, wherein the spatialized binaural audio signal is generated by using a default set of HRTFs or by using a set of generic HRTFs selected from a plurality of pre-sets such that a selected set of HRTFs matches best with the user's perception or by using a set of HRTFs measured using the binaural hearing system worn by the user and an accessory device.

12. The method of claim 1, wherein fitting parameters of the present fitting configuration include an amount of wide dynamic range compression, as determined by at least one of compression kneepoints, a beamformer pattern, an amount of noise reduction, or an amount of reverberation reduction.

13. The method of claim 1, wherein at least one of the generating of the spatialized binaural audio signal representative of the virtual auditory scene; the estimating, from the measured head movements, the user's ability of spatial sound identification with the present fitting configuration of the binaural hearing system; or the maintaining or modifying of the present fitting configuration based on the estimated user's ability of spatial sound identification with the present fitting configuration are performed on an accessory device communicatively coupled with binaural hearing system.

14. A self-fitting arrangement, comprising:

a binaural hearing system comprising a first hearing device including a first output transducer for stimulating a first ear of a user and a second hearing device including a second output transducer for stimulating a second ear of the user, the binaural hearing system further comprising at least one motion sensor; and an accessory device communicatively coupled to the binaural hearing system;

wherein the accessory device is configured to:

implement a present fitting configuration in the binaural hearing system by setting respective parameters in the binaural hearing system; and generate a spatialized binaural audio signal representative of a virtual auditory scene including at least a first audio source arranged at a given angular position relative to the user and an instruction audio signal instructing the user to turn the user's head towards the first audio source, and a second audio source arranged at an additional given angular position relative to the user and an additional instruction audio signal instructing the user to turn the user's head towards the second audio source;

wherein the binaural hearing system is configured to reproduce the spatialized binaural audio signal, the instruction audio signal, and the additional instruction audio signal to the user; and wherein the accessory device is further configured to measure respective head movements of the user via the at least one motion sensor, determine, from the measured head movements, a deviation between the measured head movements and expected head movements corresponding to the angular positions of the first audio source and the second audio source in the virtual auditory scene;

estimate from the measured head movements the user's ability of spatial sound identification with the present fitting configuration of the binaural hearing system, the estimating of the user's ability of spatial sound identification including estimating the user's ability of spatial sound segregation based on the determined deviation and a variation of an angle between the first audio source and the second audio source so as to determine a minimum angular separation at which the user perceives the first audio source and the second audio as separate sound sources; and maintain or modify the present fitting configuration based on the estimated user's ability to of spatial sound identification.

* * * * *